(12) United States Patent
Ganeev et al.

(10) Patent No.: US 6,545,756 B1
(45) Date of Patent: Apr. 8, 2003

(54) METHOD FOR THE THERMIONIC ATOMIZATION OF A SAMPLE AND DEVICE FOR REALIZING THE SAME

(76) Inventors: Alexandr Akhatovich Ganeev, 189620, Russian Federation, S-Petersburg, Pushkin, Leningradskaja Street Home 93 Appartm.22 (RU); Sergei Evgenievich Sholupov, 197341, Russian Federation, S-Petersburg, Prospekt Koroleva Home 15/30 Appartm.28 (RU)

(*) Notice: Subject to any disclaimer, the term of this patent is extended or adjusted under 35 U.S.C. 154(b) by 0 days.

(21) Appl. No.: 09/787,634
(22) PCT Filed: Sep. 21, 1998
(86) PCT No.: PCT/RU98/00294
§ 371 (c)(1), (2), (4) Date: Mar. 20, 2001
(87) PCT Pub. No.: WO00/17628
PCT Pub. Date: Mar. 30, 2000
(51) Int. Cl.$^7$ ................................................ G01J 3/30
(52) U.S. Cl. ................... 356/312; 356/314; 356/311
(58) Field of Search ....................... 356/312, 314, 356/311, 316; 256/288

(56) References Cited

U.S. PATENT DOCUMENTS 3,809,479 A * 5/1974 Whelan ..................... 356/85
4,407,582 A * 10/1983 Woodriff .................... 356/312

FOREIGN PATENT DOCUMENTS

DE 3429765 A1 2/1986
RU 2032167 C1 3/1995

OTHER PUBLICATIONS

A.N. Zaidel et al, Tekmika I prktika spektroskopii M., "Mauka", Glavenaya redaktsye fiziko–matermaticheskoi literatury, 1972, pp. 269–270.

* cited by examiner

Primary Examiner—Cassandra Spyrou
Assistant Examiner—Leo Boutsikaris
(74) Attorney, Agent, or Firm—Christopher L. Parmelee; Walker & Jocke LPA

(57) ABSTRACT

The present invention pertains to the construction of analytic instruments and can be used for analyzing natural and industrial water, biological samples, geological samples and air. The purpose of this invention is to reduce substantially the power used by the atomizer and the analyzer, and to increase the number of objects that can be analyzed. To this end, the method for the thermionic atomization of a sample involves carrying out an ionic sputtering of the sample from the cathode in a low-pressure discharge. The cathode is heated by the discharge to a temperature of between 800 and 1400° C., while the ballast gas consists of Kr or Xe under a gas pressure of 10 to 15 torrs. The thermionic atomization device includes an atomizer arranged in a gas-discharge chamber filled with an inert gas. The atomizer is made in the form of a hollow, cylindrical, metallic and thin-wall cathode. In order to reach this goal, the method involves using a thermionic atomization device which, in an efficient embodiment, consists of the above-mentioned gas-discharge atomizer, i.e. a hollow, metallic and thin-wall cathode. This mechanism enables the sputtering and atomization of the sample in a short time (0.2 to 1 sec.), thus lowering the detection limits while eliminating matrix effects.

20 Claims, 5 Drawing Sheets

Figure 1:
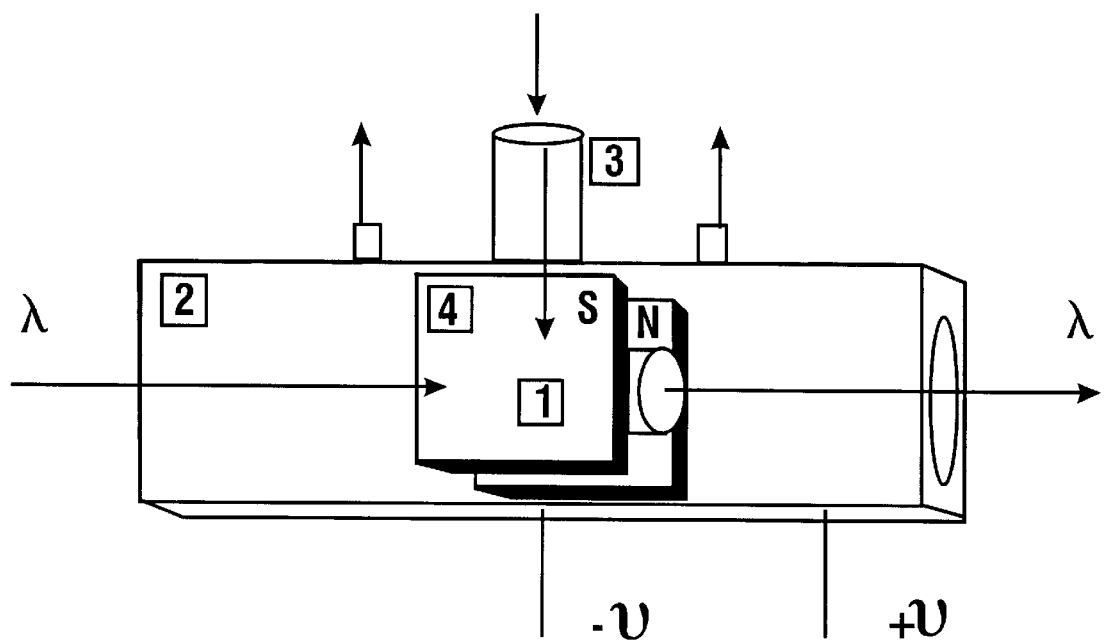

The scheme of the Glow Discharge Atomizer.

Calibration curves for Ag, Cu, Mn and Pb.

Analytical signals for Pb (curve 1) Mn (2), Cu (3) in blood.
Curves 4 and 5 - background absorption for Cu and Mn.

Analytical signals (curves 1 and 2) and background absorption (3 and 4) for lead in urine. Curves 1 and 3 - employee of St. Petersburg State University, 2 and 4 - employee of Battery plant.

METHOD FOR THE THERMIONIC ATOMIZATION OF A SAMPLE AND DEVICE FOR REALIZING THE SAME

FIELD OF TECHNIQUE

The invention refers to analytical instrument engineering and can be used for analyses of natural and process water, biological and geological samples and air.

PREVIOUS TECHNICAL LEVEL

The known method of sample atomization is evaporation of the sample in a heated electro-thermal atomizer with subsequent dissociation of evaporated compounds in the gas phase at a temperature of 2000–3000° C. [1].

The disadvantage of this method is high consumption of power and presence (in case of atomization of samples having a complicated base) matrix and spectral influences.

Other known methods are atomization in a cooled [2] or a hot [3] hollow cathode. Cathode spraying of the wall material by ions of the ballast gas with energy 100–3000 eV in the discharge with cooled hollow cathode in used mainly for analyses of solid specimens and the in layers analyses. In case of a hot hollow cathode the process of conversion of atoms into the gas phase is mainly determined by thermal evaporation.

The disadvantages of the known methods are: if the above mentioned types of discharges are considered from the point of using them for gas discharge atomization of the sample it will be found that both the cooled and the hot hollow cathode cannot be competitive atomizers as the rate of spraying in the cooled hollow cathode is very low—the period of complete spraying of a sample amounts scores of minutes and hours. As to the hot hollow cathode rate of atomization of a sample is determined exclusively by thermal evaporation (due to the ejection of the field by thermo-emission electrons)—the process which is sufficiently efficient only at temperatures of 2000–2800° C. In this case it is preferable to use a usual electro-thermal atomizer operating at atmospheric pressure as the retentivity period of this device is greater than that of the hot hollow cathode and atomization power is comparable [1].

Functionally the closest to the proposed method is the method of atomization by ionic spraying a sample form the surface of the cold flat cathode (the Grimm's discharge) in the low pressure discharge spraying by comparatively high ionic amperage (to 1A). In this case the sample spraying rate is rather high—the period of spraying is about 0.3–2 sec. According to this method sprayed atoms are transferred by the gas flow or due to diffusion out of the spraying zone into the analytic zone through which analytic resonance radiation passes [4].

The disadvantages of this method are low maximal volumes of a liquid sample not in excess of 1 mcl which results in low concentration limits of detection—no more than 10 mcg/l. Besides the known method cannot be used with the high selectivity method of correction of non-selective absorption which besides considerable matrix effects an the influence of the atomizer glow on the results of analyses does not make it possible to analyze samples of complicated composition, particularly bio- and geological samples. Comparatively high power consumed in the process of atomization in the Grimm's discharge (300 W) prevents from development of a mobile analyzer based on the known method for in-situ determination of elements in water and in the air.

An atom-absorption electro-thermal atomizer is known in the shape of a graphite tube with a dosage opening, heated by electric current [2]. In this device atomization is effected by thermodynamically equalized processes of dissociation of compounds evaporated during the heating of the atomizer.

The disadvantage of the known method is high power consumption and presence of matrix and spectral influences (in case of atomization of samples having a complicated base). From technical point of view the closest to the proposed device is the flat gas discharge atomizer (Grimm's discharge) in which analyzed atoms are transferred by the gas flow or due to diffusion out of the spraying zone into the analytical zone through which the resonance radiation passes [4].

The disadvantages of this method are low maximal volumes of a liquid sample not to exceed 1 mcl which results in low concentration limits of detection—no more than 10 mcg/l. Besides comparatively high power consumed by the known device (300 W) prevents from using it as a mobile analyzer intended for in-situ determination of elements in water and in the air.

The closest to the proposed analyzer in technical respect is the Seeman's atom absorption analyzer that contains a source of resonance radiation, a polarizer, optoacoustic modulator, and inclined plate, a phase plate, an atomizer placed in the transverse magnetic field, a polarizing compensator, a monochromator, a photodetector the signal from which is detected in the recording system and is transmitted to the computer [3].

The disadvantage of the known device is high power consumption which restricts the possibilities of the known device. Besides considerable matrix effects not only hamper but often make direct analysis of samples with complicated composition impossible.

The purpose of the invention is to considerably reduce power consumed by the atomizer and the analyzer and to extend the scope of objects accessible for analyses.

This aim is reached by:

1. According to the proposed method of sample atomization including ionic spraying the sample from the cathode in the low pressure discharge the cathode is heated by the discharge to a temperature of 800–1400° C.; Kr or Xe is used as the ballast and the gas pressure range is 10–15 tors.
2. The device for ionic-thermal atomization of the sample includes an atomizer placed into the gas discharge chamber filled with inert gas the atomizer being made in the shape of the thin-walled metal cylindrical hollow cuvette (thin-walled metal cylindrical hollow cathode).

To solve the problem the proposed method includes the ionic-thermal mechanism of atomization. This mechanism enables to spray and atomize a sample within a small period of time (0.2–1 sec) which makes it possible to reach low limits of detection without matrix effects. The ionic-thermal mechanism of atomization realized efficiently in the proposed gas discharge atomizer—the thin walled metal hollow cathode (TMHC), is connected with combined influence of the temperature of TMHC, mass and energy of spraying ions on the rate of spraying.

Let us consider one of the possible ways of realization of the proposed method in which TMHC is one of the components of the atom-absorption analyzer based on the method of differential absorption analysis—Seeman's modulation polarizing spectroscopy with high frequency modulation (SMPSHFM) [5].

The design of the proposed atomizer is shown in FIG. 1. It consists of TMHC (1), discharge tube (2) port for filling in samples (3), permanent magnet (4). Discharge tube (2) is the anode and is earthed.

Figure 2:
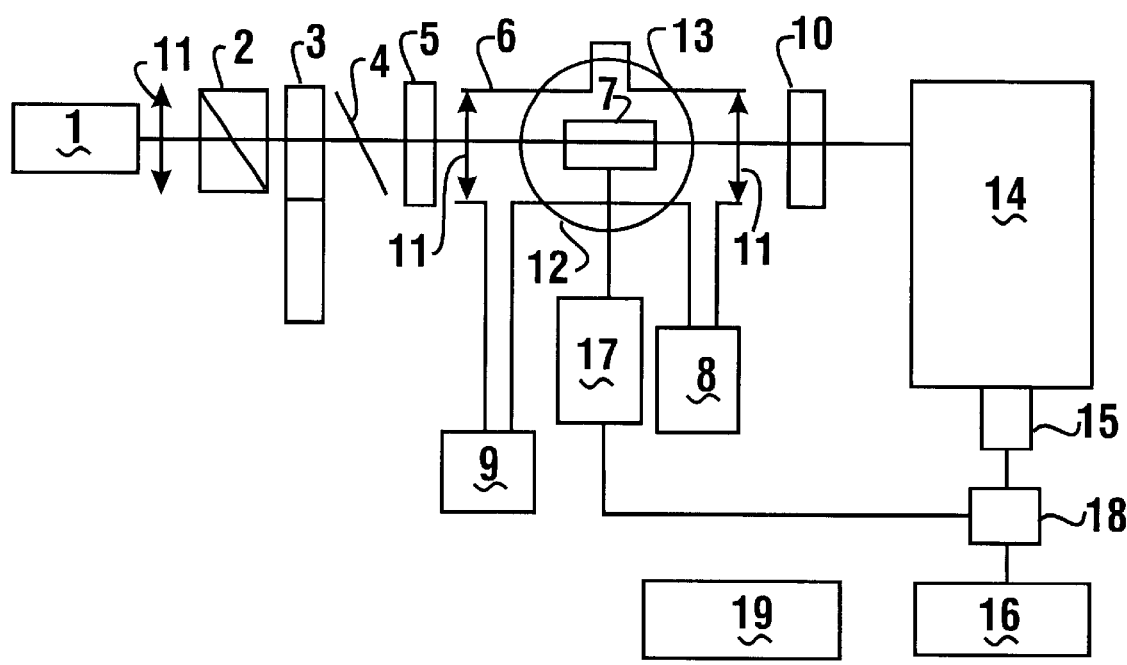

The proposed analyzer is shown in FIG. 2. Here 1—the source of resonance radiation, 2—polarizer, 3—optoacoustic modulator, 4—inclined plate, 5—phase plate, 6—gas discharge chamber, 7—thin-walled metal hollow cathode, 8—ballast gas supply system, 9—discharge system, 10—polarization compensator, 11—lenses, 12—magnet, 13—vacuum valve intended for filling in the sample, 14—monochromator, 15—photo diode, 16—system of recording variable signals at the frequency of the first harmonica of the optoacoustic modulator (50 kHz) and the second harmonica (100 kHz), 17—pulse power supply system of TMHC, 18—electronic switch, 19—computer.

TMHC is a cylinder 5 mm in diameter, 10 mm in length, wall thickness of walls 50 mcm. Material of TMHC—tungsten or molybdenum. Computer 19 (PC 386 or higher) is in this case the recording and processing device.

The process of analysis is effected in the following way (see FIG. 2). The sample of the liquid to be analyzed is filled in through vacuum valve (13) and the upper dosage opening (in experiments not only water solutions and biological samples but also organic liquids—benzene and condensed gas were analyzed). After closing the valve gas is pumped out of the TMHC (7) with simultaneous filling in the ballast gas.

Pumping rate is 2–4 ml/min on conversion to atmospheric pressure. 1 min after commencement of pumping out to destroy the sample matrix a weak pulse discharge with mean amperage 5 mA is switched on for 10 sec (if necessary). Without preliminary weak discharge the period of drying the sample lasts 3–5 min. On completion of drying the atomizing discharge is switched on—current pulse 160–300 mA, mean amperage 30–100 mA, mean wattage 30–70 W, voltage of the pulse power supply system of TMHC—800–1400 V, voltage of TMHC—600–900 V. Calculated and measured experimentally optimal value of the magnet field intensity (at which differential adsorption section is maximal) for such elements as Cu, Ag, POB, Au, Mn is within the range 2.5–3.5 kE. Hence permanent magnet field with intensity 3 kE may be used in the analyzer.

For selective detection of atoms differential atom absorption analysis method—Seeman's modulation polarizing spectroscopy with high frequency modulation (SMPSHFM) is used. According to this method signals are detected at the frequency of the first harmonic $S_1$ and the second harmonic $S_2$ of the optoacoustic modulator. The first of them is proportional to the difference in absorption of analytical and bearing radiation and the second one—to the radiation intensity. The resulting integral analytical signal $S_i$ is equal to:

$$S_i = \int S \, dt = -\frac{b}{2} \int \mathrm{Ln} \frac{b - \frac{S_1}{S_2}}{b + \frac{S_1}{S_2}} \, dt$$

where b—graduation constant, S—analytical signal registered at moment t. As modulation frequency in the SMPSHFM method is considerably higher than the frequency of atomizing pulses, ON or OFF switching of electronic switch 18 reduces the mean value of the signal at the frequency of the $2^{nd}$ harmonic of the optoacoustic modulator proportional to the intensity of the radiation source making no disturbances in recording the differential signal at the frequency of the $1^{st}$ harmonic. At the same time the use of the electronic switch eliminates the influence of discharge glow that increases considerably noise levels and restricts limits of detection.

High concentration of charged particles in the discharge and high energy of ions (100–300 eV) causes efficient dissociation of compounds in the gas phase which reduces considerably both matrix effects and non-selective adsorption. Besides still not investigated but very efficient mechanism of atomization—the so called ionic-thermal spraying is realized in TMHC. This mechanism operates in the event that two factors are available: relatively moderate temperature of TMHC—about 1000–1400° C. and moderate ion currents. In this case sample spraying rate is very high—the relevant period of atomization of the sample for such elements as Cu, Ag, Pb, Au, Mn is within the range 0.2–2 sec. At a temperature of >1500° C. high thermo-electron emission from a cathode results in ejection of the field out of the cathode which reduces the energy of spraying ions. In this case the process of evaporation and atomization of the sample is purely thermal and the period of atomization of the sample increases considerably. Therefore the range of temperature 1000–1400° C. is optimal.

High temperature gradient near the ends of TMHC results in generation of peculiar diffusion traps for atoms to be analyzed. Presence of traps increases considerably time of keeping atoms in the analytical zone which results in increase of sensitivity of the analyzer.

Optimal pressure of the ballast gas is determined by two factors, Dependence of analytical signal S on pressure of the ballast gas as measured in the process of the experiment was linear. The time of keeping atoms in TMHC and hence the value of the analytic signal was directly proportional to pressure. At the same time at pressure of the ballast gas in excess of 13–14 tors the discharge became unstable. Therefore pressure of 12 tors was selected as optimal.

The kind of the ballast gas plays a considerable part in the process of atomization. The transition from light inert gases to heavy ones reduces the diffusion factor which increases the time of confinement of atoms and sensitivity. Besides the increase of mass of the ballast gas atoms and corresponding increase of mass of spraying ion increases considerably the rate of spraying which reduces the limit of detection, Therefore in this case Kr and Xe are optimal gases.

Figure 3:
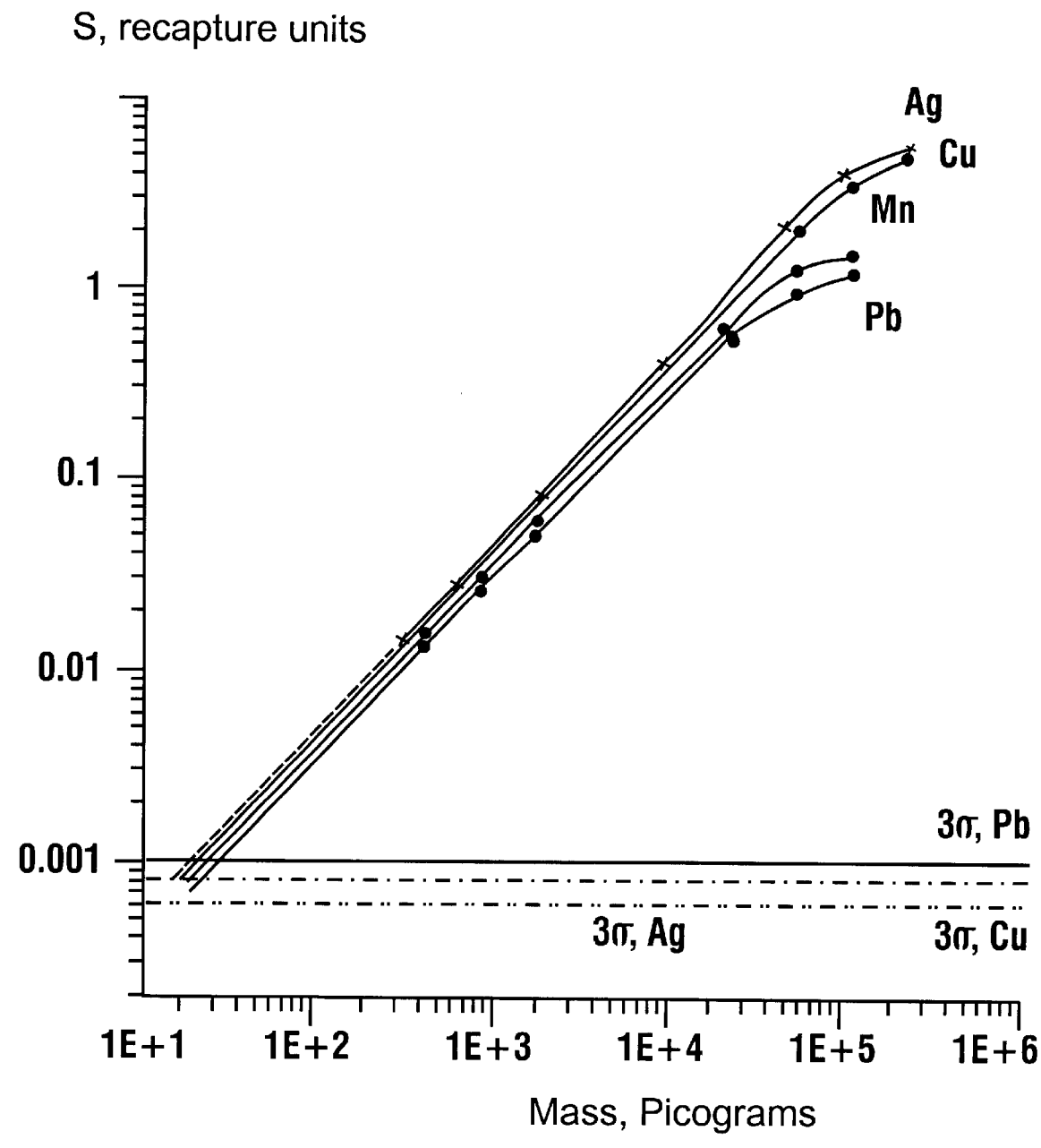
Figure 4:
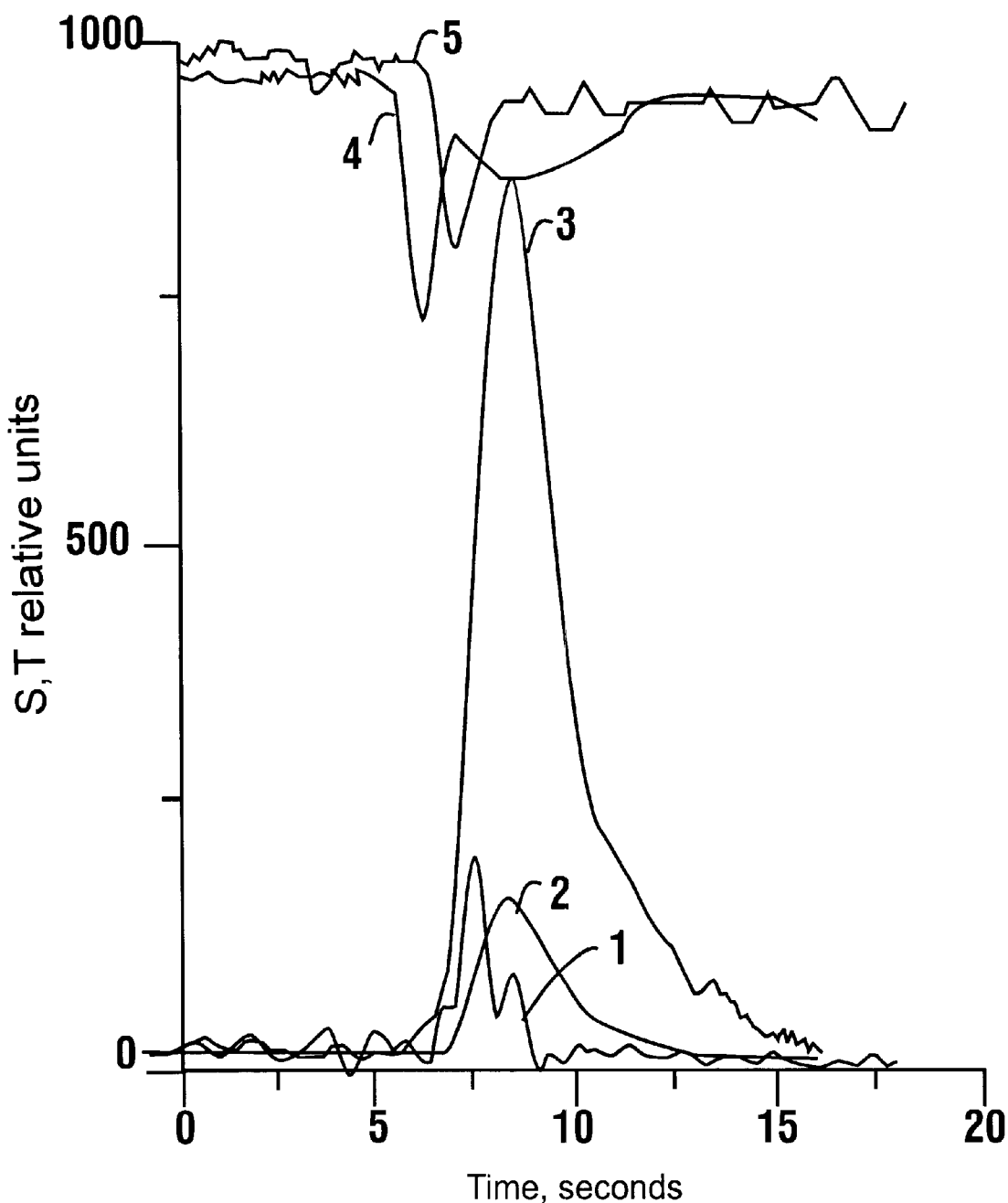
Figure 5:
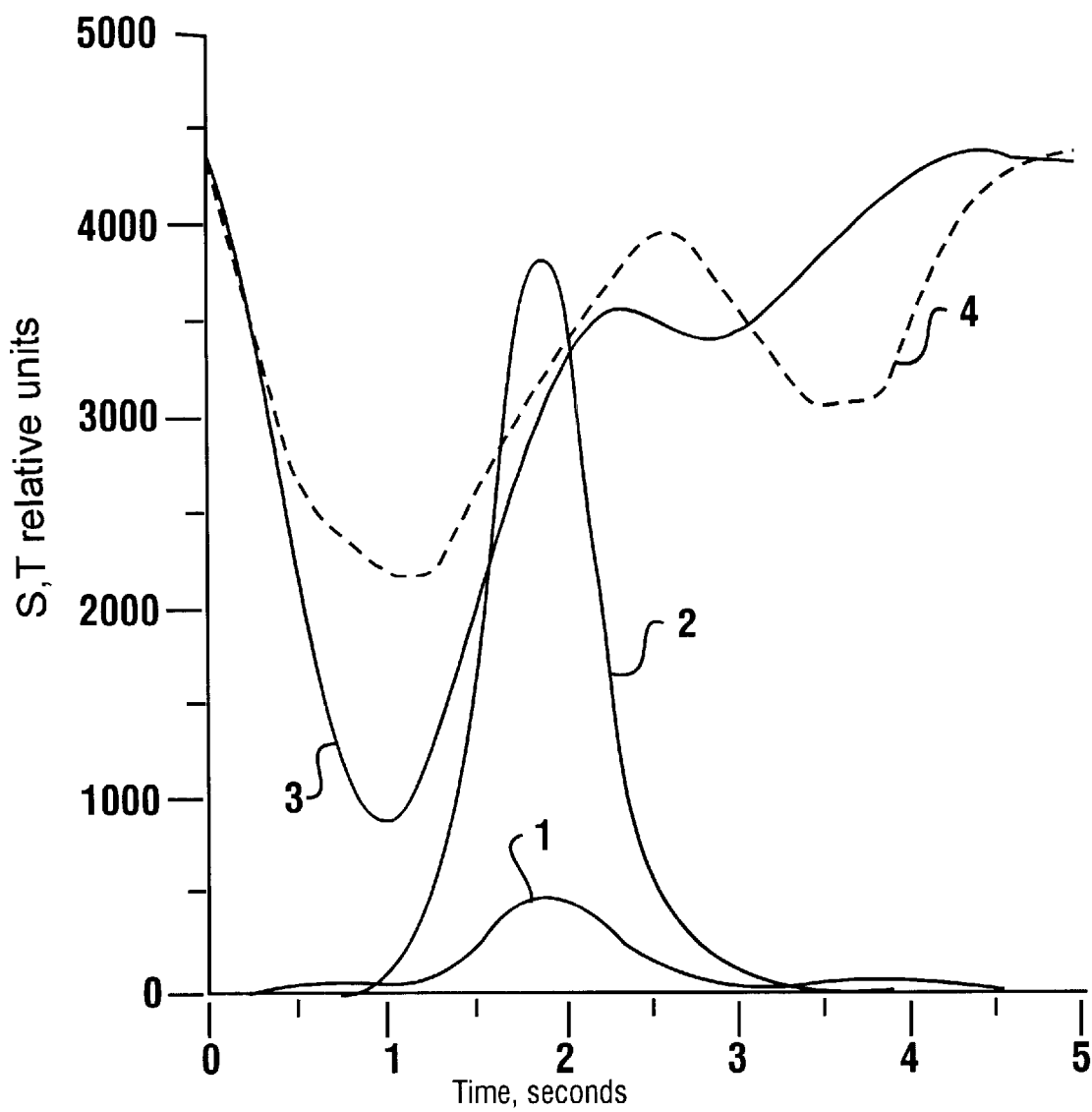

Relevant graduation curves are shown in FIG. 3, analytical signals S obtained when determining lead, manganese, and copper in blood are shown in FIG. 4; signals S when determining lead in urine of an employee of the State University in St.Petersburg (curve 1) and of an employee of the Battery works (curve 2) are shown in FIG. 5. Transmission T versus time curves are also shown in FIG. 4 and 5. Table 1 contains comparative limits of detection of the proposed analyzer, MFA-911 analyzer with a graphite oven and the same method of correction of non-selective adsorption —SMPSHFM as in the proposed analyzer (the prototype) and ZL 4100 analyzer with a graphite oven and a longitudinal modular magnet field (manufactured by the Perkin-Elmer Co). As it can be seen from the table the detection limits for the analyzer proposed and the analyzer with a graphite oven are comparable but at the same time the proposed analyzer due to low power consumption and possibility to handle complicated samples can be used as a base for development of a series of analyzers intended for in-situ operation.

TABLE I

| Element | proposed analyzer | MT A-911 | ZL 4100 |
|---|---|---|---|
| Ag | 6 | 3 | 3 |
| Cu | 8 | 3 | 4 |
| Mn | 18 | 6 | 5 |
| Pb | 12 | 4 | 4 |

REFERENCES

1. W. Slawin Graphite Furnace AAS. A Source Book. Perkin-Elmer, Norfolk, Conn., 1984.
2. W. W. Harrison, C. W. Barchick J. A. Klinger, P. H. Patliff and Y. Mei, Anal. Chem. 62 (1990) 934A.
3. O. S. Lunyov and S. V. Oshemkov, Spectrochim, Acta Part B, 47 (1992) 71.
4. C. L. Chacrabarti, K. L. Headrick, J. C. Hutton, P. C. Bertels and M. H. Back // Spectrochim Acta, 1991, 46B, P.183–190.
5. A. A. Ganeev, S. E. Sholupov, A. D. Timofeev, V. M. Ivankov //OKAX 1995. T.50. C.683–689.

SUMMARY OF THE INVENTION

1. Method of ionic—thermal atomization of a sample that includes ionic spraying of the sample from the cathode in the low pressure discharge, which is distinguished by the fact that the cathode is heated by the discharge to a temperature of 800–1400° C.; Kr or Xe is used as a ballast gas the gas pressure range being 10–15 tors.

2. The device for ionic—thermal atomization comprises the atomizer placed into the gas discharge chamber filled with inert gas, which is distinguished by the fact that the atomizer is made in the shape of a metal cylindrical hollow cathode.

What is claimed is:

1. A method of ionic-thermal atomization of a sample comprising:
    a) placing a sample within a cathode arranged inside a gas-discharge chamber;
    b) filling the discharge chamber with an inert gas at a pressure between 10 torr and 15 torr;
    c) causing ionic sputtering of the sample from the cathode by discharging an electrical current, wherein the discharge of the electrical current is operative to heat the cathode to a temperature between 800° C. and 1400° C.; and
    d) analyzing the atoms sputtered from the sample.

2. An ionic-thermal atomization device comprising:
    a discharge chamber;
    a cathode positioned within the gas-discharge chamber, wherein the cathode is operative to receive a sample therein;
    a supply of an inert gas in fluid communication with the cathode, wherein the supply is operative to fill the cathode with the inert gas at a pressure between 10 torr and 15 torr; an electrical current source in operative connection with the cathode, wherein the electrical current source is operative to discharge an electrical current which is operative to heat the cathode to a temperature between 800° C. and 1400° C.; and
    an analysis device in operative connection with the gas-discharge chamber, wherein the analysis device is operative to analyze atoms sputtered from the sample.

3. The device according to claim 2, wherein the cathode is comprised of a metal and has a generally cylindrical hollow shape.

4. The device according to claim 3, wherein the metal is selected from the group consisting of tungsten and molybdenum.

5. The device according to claim 4, wherein the cathode includes walls with a thickness of about 50 mcm.

6. The device according to claim 5, wherein the cathode has a length of about 10 mm and a diameter of about 5 mm.

7. The device according to claim 2, wherein the electrical current source is operatively configured to discharge the electrical current with a mean amperage of between 30 mA to 100 mA and a mean wattage of between 30 W and 70 W for a period of time between 0.2 seconds and 1.0 seconds.

8. The device according to claim 2, wherein the analysis device is operative to perform Seeman's modulation polarizing spectroscopy with high frequency modulation.

9. The device according to claim 8, further comprising a magnet, wherein the magnet is operative to direct a magnetic field through the cathode with an intensity of between about 2.5 kE and 3.5 kE.

10. The method according to claim 1, wherein in step (a) the cathode is comprised of a metal and has a cylindrical hollow shape.

11. The method according to claim 10, wherein the metal is selected from the group consisting of tungsten and molybdenum.

12. The method according to claim 11, wherein the cathode includes walls with a thickness of about 50 mcm.

13. The method according to claim 12, wherein the cathode has a length of about 10 mm and a diameter of about 5 mm.

14. The method according to claim 1, wherein in step (d) the sample is analyzed using Seeman's modulation polarizing spectroscopy with high frequency modulation.

15. The method according to claim 14, wherein in step (c) the cathode lies within a magnetic field with an intensity of between about 2.5 kE and 3.5 kE.

16. The method according to claim 1, wherein in step (c) the discharge of the electrical current occurs for a period of time between 0.2 seconds and 1.0 seconds.

17. The method according to claim 1, wherein the discharge of electrical current has a mean amperage of between 30 mA and 100 mA and a mean wattage of between 30 W and 70 W.

18. The method according to claim 17, wherein between steps (b) and (c) further comprising:
    e) drying the sample, including discharging an electrical current with a mean amperage of about 5 mA.

19. The method according to claim 1, wherein in step (b) the inert gas includes at least one gas selected from the group consisting of Kr and Xe.

20. The method according to claim 19, wherein step (b) includes pumping existing gases out of the cathode.

* * * * *